(12) United States Patent
Yao et al.

(10) Patent No.: US 7,273,893 B2
(45) Date of Patent: Sep. 25, 2007

(54) PROCESS FOR CONVERTING CARBON DIOXIDE TO OXYGENATES

(75) Inventors: Jianhua Yao, Bartlesville, OK (US); James B. Kimble, Bartlesville, OK (US)

(73) Assignee: ConocoPhillips Company, Houston, TX (US)

(*) Notice: Subject to any disclaimer, the term of this patent is extended or adjusted under 35 U.S.C. 154(b) by 643 days.

(21) Appl. No.: 10/683,974

(22) Filed: Oct. 10, 2003

(65) Prior Publication Data

US 2004/0092610 A1   May 13, 2004

Related U.S. Application Data

(63) Continuation of application No. 09/963,831, filed on Sep. 26, 2001, now Pat. No. 6,664,207.

(51) Int. Cl.
*C07C 27/00* (2006.01)
*C07C 41/00* (2006.01)

(52) U.S. Cl. ......................... 518/713; 568/671

(58) Field of Classification Search ................ 518/713; 568/671; 502/61, 64, 67
See application file for complete search history.

(56) References Cited

U.S. PATENT DOCUMENTS

| | | | |
|---|---|---|---|
| 3,928,483 A | | 12/1975 | Chang et al. |
| 4,011,275 A | | 3/1977 | Zahner |
| 4,046,830 A | * | 9/1977 | Kuo .............................. 208/64 |
| 4,086,262 A | * | 4/1978 | Chang et al. ................ 518/716 |
| 4,279,830 A | * | 7/1981 | Haag et al. .................. 518/700 |
| 4,341,069 A | | 7/1982 | Bell et al. |
| 4,349,464 A | | 9/1982 | Wainwright et al. |
| 4,423,155 A | | 12/1983 | Bell et al. |
| 4,444,909 A | * | 4/1984 | Chang et al. ................ 518/716 |
| 4,487,984 A | | 12/1984 | Imai |
| 4,543,347 A | | 9/1985 | Heyward et al. |
| 4,590,176 A | | 5/1986 | Hoek et al. |
| 4,665,042 A | * | 5/1987 | Budge et al. .................. 502/61 |
| 4,751,248 A | | 6/1988 | Lin et al. |
| 4,950,821 A | | 8/1990 | Ratnasamy et al. |
| 5,004,717 A | | 4/1991 | Lee et al. |
| 5,096,688 A | | 3/1992 | Miller et al. |
| 5,300,695 A | | 4/1994 | Radlowski |

FOREIGN PATENT DOCUMENTS

JP   2001-070793   * 3/2001

OTHER PUBLICATIONS

Machine translation of JP 2001-070793, pp. 1-6, Mar. 21, 2001.*
Translation of Japan 2001-070793, Mar. 21, 2001.*

* cited by examiner

*Primary Examiner*—Steven Bos
(74) *Attorney, Agent, or Firm*—Ryan N. Cross; Kameron D. Kelly

(57) ABSTRACT

A catalyst and process for converting carbon dioxide into oxygenates. The catalyst comprises copper, zinc, aluminum, gallium, and a solid acid.

39 Claims, No Drawings

PROCESS FOR CONVERTING CARBON DIOXIDE TO OXYGENATES

RELATED APPLICATIONS

This is a continuation of application Ser. No. 09/963,831, filed Sep. 26, 2001, entitled CATALYST FOR CONVERTING CARBON DIOXIDE TO OXYGENATES AND PROCESSES THEREFORE AND THEREWITH, which issued as U.S. Pat. No. 6,664,207 on Dec. 16, 2003, and is hereby incorporated by reference.

BACKGROUND OF THE INVENTION

1. Field of the Invention

The present invention relates generally to the conversion of carbon dioxide to oxygenates. In another aspect, the invention concerns a catalyst for converting a feed comprising carbon dioxide and hydrogen into methanol and dimethyl ether.

2. Discussion of Prior Art

Carbon dioxide for industrial use is typically recovered from synthesis gas production, substitute-natural gas production, cracking of hydrocarbons, and natural springs or wells. Although carbon dioxide can be used for numerous purposes such as, for example, refrigeration, carbonating beverages, and as an aerosol propellent, in certain situations it may be more desirable to convert carbon dioxide to other higher-value compounds such as oxygenates.

Oxygenates can be used for a variety of purposes such as, for example, enhancing of motor fuel octane and improving the emissions quality of motor fuel. Methanol and dimethyl ether are two oxygenates which can be of particularly high value. Methanol can be used for a variety of purposes including, for example, as an alternative motor fuel, as an intermediate in the production of high octane ethers (e.g., MTBE), and as a fuel for fuel cell driven vehicles. Dimethyl ether is also useful for a variety of purposes including, for example, as an alternative motor fuel, as a starting material towards the synthesis of various hydrocarbons, as a fuel additive to lower emissions, and as an aerosol propellent.

Although it is known that synthesis gas comprising carbon monoxide, carbon dioxide, and hydrogen can be converted into oxygenates using a copper-containing catalyst, there exists a need for a catalyst which is effective to convert carbon dioxide into oxygenates with increased carbon dioxide conversion as well as increased product selectivity towards methanol and dimethyl ether, particularly dimethyl ether.

OBJECTS AND SUMMARY OF THE INVENTION

An object of the present invention is to provide a catalyst and process for converting carbon dioxide to oxygenates wherein there is an increased carbon dioxide conversion.

A further object of the present invention is to provide a catalyst and process for converting carbon dioxide to oxygenates wherein there is an increased product selectivity towards methanol and dimethyl ether.

A still further object of the present invention is to provide a catalyst and process for converting carbon dioxide to oxygenates wherein there is an enhanced product selectivity towards dimethyl ether versus methanol.

An even further object of the present invention is to provide a catalyst and process for converting carbon dioxide to oxygenates wherein the amount of carbon monoxide produced is minimized.

A yet further object of the present invention is to provide a novel process for preparing a catalyst effective to convert carbon dioxide into oxygenates.

It should be noted that not all of the above-listed objects need be accomplished by the invention claimed herein and other objects and advantages of this invention will be apparent from the following description of the invention and appended claims.

In accordance with one embodiment of the present invention, a catalyst composition is provided. The catalyst composition comprises copper, zinc, aluminum, gallium, and a solid acid.

In accordance with another embodiment of the present invention a catalyst composition for converting carbon dioxide to methanol and dimethyl ether is provided. The catalyst composition comprises reduced-valence copper, zinc oxide, aluminum oxide, gallium oxide, and a zeolite having an acid function.

In accordance with another embodiment of the present invention, a method of making a catalyst composition is provided. The method comprises the steps of: (a) combining a copper-containing compound, a zinc-containing compound, an aluminum-containing compound, a gallium-containing compound, and a solid acid compound to form a catalyst mixture; (b) calcining the catalyst mixture to form a calcined catalyst; and (c) reducing the calcined catalyst to form a reduced catalyst.

In accordance with a still further embodiment of the present invention, a process for converting a carbon dioxide-containing feed into oxygenates is provided. The process comprises the steps of: (a) contacting the carbon dioxide-containing feed with a catalyst composition comprising copper, zinc, aluminum, gallium, and a solid acid in a reaction zone under reaction conditions sufficient to convert at least a portion of the carbon dioxide-containing feed into oxygenates; and (b) recovering of at least a portion of the oxygenates from the reaction zone.

DETAILED DESCRIPTION OF THE PREFERRED EMBODIMENTS

In accordance with the first embodiment of the present invention a catalyst comprising copper, zinc, aluminum, gallium, and a solid acid is provided.

The copper component of the inventive composition can exist in the form of any copper-containing compound such as, for example, elemental copper, copper oxide, and/or a copper oxide precursor. It is preferred for the inventive catalyst composition to contain from about 2 to about 50 weight percent copper based on the total weight of the catalyst composition, more preferably from about 10 to about 35 weight percent copper, most preferably from 20 to 30 weight percent copper. At least a substantial portion of the copper component is preferably present in the inventive catalyst composition in a reduced-valence state. The valence of the copper in the reduced-valence state (i.e., the reduced-valence copper) is less than the valence of copper in its common oxidized state, preferably less than two, most preferably zero. It is preferred that at least about 20 weight percent of the copper present in the inventive catalyst composition be present in the reduced-valence state, more preferably at least about 60 weight percent of the copper is present in the reduced-valence state, and most preferably at least 80 weight percent of the copper is present in the reduced-valence state.

The zinc component can exist in the form of any zinc-containing compound such as, for example, elemental zinc, zinc oxide, and/or a zinc oxide precursor. Preferably, the zinc component comprises zinc oxide. It is preferred for the inventive composition to contain from about 1 to about 40 weight percent zinc based on the total weight of the catalyst composition, more preferably from about 5 to about 30 weight percent zinc, most preferably from 10 to 20 weight percent zinc. The weight ratio of zinc to copper in the inventive catalyst composition is preferably from about 0.01:1 to about 10:1, more preferably from about 0.1:1 to about 5:1, and most preferably from 0.4:1 to 0.8:1.

The aluminum component can exist in the form of any aluminum-containing compound such as, for example, elemental aluminum, aluminum oxide, and/or an aluminum oxide precursor. Preferably, the aluminum component comprises aluminum oxide. It is preferred for the inventive catalyst composition to contain from about 0.5 to about 25 weight percent aluminum based on the total weight of the catalyst composition, more preferably from about 1 to about 15 weight percent aluminum, and most preferably from 2 to 5 weight percent aluminum. The weight ratio of aluminum to copper in the inventive catalyst composition is preferably from about 0.01:1 to about 5:1, more preferably from about 0.05:1 to about 1:1, and most preferably from 0.1:1 to 0.2:1.

The gallium component can exist in the form of any gallium-containing compound such as, for example, elemental gallium, gallium oxide, and/or a gallium oxide precursor. Preferably, the gallium component comprises gallium oxide. It is preferred for the inventive catalyst composition to contain from about 0.1 to about 15 weight percent gallium based on the total weight of the inventive catalyst composition, more preferably from about 0.5 to about 10 weight percent gallium, and most preferably from 1 to 3 weight percent gallium. The weight ratio of gallium to copper in the inventive catalyst composition is preferably from about 0.005:1 to about 5:1, more preferably from about 0.01:1 to about 1:1, and most preferably from 0.05:1 to 0.2:1.

The "solid acid" of the inventive composition is defined herein as being any solid compound which exhibits an acid function (i.e., functions as a proton donor). Preferably, the solid acid is a zeolite. More preferably, the solid acid is a zeolite having a constraint index (as defined in U.S. Pat. No. 4,097,367, which is incorporated herein by reference) in the range of from about 0.4 to about 12, preferably from 2 to 9. Generally, the molar ratio of $SiO_2$ to $Al_2O_3$ in the crystalline framework of the preferred solid acid zeolite is about 5:1 and can range up to infinity. Preferably, the molar ratio of $SiO_2$ to $Al_2O_3$ in the preferred solid acid zeolite framework is from about 5:1 to about 200:1, more preferably from 40:1 to 70:1. Preferred solid acid zeolites include ZSM-5, ZSM-8, ZSM-11, ZSM-12, ZSM-35, ZSM-38, and mixtures thereof. The preferred solid acid zeolites can also be described as crystalline aluminosilicates. Suitable aluminosilicates generally have a medium pore size, generally being an effective fine porous size of from about 5 to about 6.5 angstroms, although small (generally 3 to 5 angstroms) or large pore (generally 7 to 8 angstroms) solid acid zeolites can also be used. ZSM-5 and similar solid acid zeolites that have been identified as having a framework topology identified as MFI are particularly preferred because of their shape selectivity. The presently most preferred solid acid is ZSM-5.

It is preferred for the inventive catalyst composition to contain from about 5 to about 80 weight percent solid acid based on the total weight of the inventive catalyst composition, more preferably from about 10 to about 60 weight percent solid acid, and most preferably from 30 to 50 weight percent solid acid. The weight ratio of solid acid to copper in the inventive catalyst composition is preferably from about 0.1:1 to about 20:1, more preferably from about 0.5:1 to about 10:1, and most preferably from 1:1 to 2:1.

The inventive catalyst composition can further comprise a binder component having binding properties which provide for a final catalyst composition having the desired physical properties. Examples of suitable binder materials include those selected from the group consisting of bentonite, aluminate, kaolin, alumina, silica, colloidal silica, sodium silicate, titania, zirconia, aluminosilicates (e.g., clays), zinc aluminate, zinc titanate, metal oxides, and any mixtures thereof. Preferred binders are selected from the group consisting of bentonite, alumina, silica, aluminosilicates, and any two or more thereof. When the inventive catalyst composition comprises a binder, it is preferred for the catalyst composition to contain from about 1 to about 40 weight percent binder based on the total weight of the inventive catalyst composition, more preferably from about 4 to about 30 weight percent binder, and most preferably from 8 to 15 weight percent binder. The weight ratio of binder to copper in the inventive catalyst composition is preferably from about 0.02:1 to about 10:1, more preferably from about 0.1:1 to about 5:1, and most preferably from 0.2:1 to 1:1.

It is preferred for the copper, zinc, aluminum, and gallium components of the inventive catalyst composition to be present in the form of a coprecipitate with the coprecipitate and the zeolite, and optionally the binder, being substantially evenly dispersed throughout the final catalyst composition.

In accordance with the second embodiment of the present invention a method of making the inventive catalyst composition of the first embodiment of the present invention is provided.

The inventive catalyst composition is preferably made, at least in part, by a coprecipitation process. The coprecipitation process can be commenced by contacting an aqueous metal-salt solution containing a copper compound, a zinc compound, an aluminum compound, a gallium compound, and water with a basic substance under suitable conditions to cause coprecipitation of the metals. After the solid coprecipitate has formed, it is allowed to age for a suitable period of time. The coprecipitate is then filtered from the remaining liquid solution, washed, dried, and calcined.

The aqueous metal-salt solution employed in the above-described coprecipitation process is preferably formed by combining soluble salts of copper, zinc, aluminum, and gallium with an appropriate amount of a suitable solvent. The soluble salts of copper, zinc, aluminum, and gallium can be, for example, nitrates, acetates, halides, or any other suitable salts known to those skilled in the art to form the desired product. Most preferably, the metal-salt solution is formed by combining copper nitrate, zinc nitrate, aluminum nitrate, gallium nitrate, and water in appropriate amounts. Preferably, the ratio of zinc to copper in the aqueous metal-salt solution is from about 0.01:1 to about 10:1, more preferably from about 0.1:1 to about 5:1, and most preferably from 0.4:1 to 1:1. Preferably, the weight ratio of aluminum to copper in the aqueous metal-salt solution is from about 0.01:1 to about 5:1, more preferably from about 0.05:1 to about 1:1, and most preferably 0.1:1 to 0.2:1. Preferably, the weight ratio of gallium to copper in the aqueous metal-salt solution is from about 0.005:1 to about 5:1, more preferably from about 0.01:1 to about 1:1, and most preferably from 0.05:1 to 0.2:1. The amount of solvent, preferably water, employed in the solution can be any amount of solvent sufficient to dissolve the metal salts. Preferably, the weight ratio of solvent to the copper in the aqueous metal-salt solution is from about 0.1:1 to about 1,000:1, more preferably from about 1:1 to about 100:1, and most preferably from 5:1 to 20:1.

The basic substance contacted with the aqueous metal-salt solution can be any substance operable to facilitate coprecipitation of a Cu/Zn/Al/Ga solid coprecipitate. The basic substance is preferably a liquid substance having a pH value of more than about 8, preferably between about 9 and 12. The basic substance preferably comprises a basic component selected from the group consisting of ammonia, carbonates, bicarbonates, and alkali metal hydroxides. Most preferably, the basic substance is an aqueous solution containing sodium bicarbonate and water, with the weight ratio of sodium bicarbonate to water in the solution being from about 0.01:1 to 10:1, most preferably from 0.05:1 to 0.2:1.

The aqueous metal-salt solution is preferably contacted with the basic solution by combining the basic substance and the metal-salt solution in a mixer. Preferably, after combining the basic substance and the metal-salt solution, the resulting solution is mixed by any suitable method known in the art for a period of about 5 minutes to about 5 hours, more preferably from about 10 minutes to about 1 hour. During mixing of the metal-salt solution and the basic substance, it is preferred that the mixed solution be maintained at a temperature of from about 10° C. to about 200° C., more preferably from about 20° C. to about 100° C., and most preferably from about 60° C. to about 80° C.

After mixing, the formed coprecipitate and liquid solution are preferably aged, without mixing, at a temperature of from about 20° C. to about 100° C. for a time period of from about 10 minutes to about 5 hours.

The solid coprecipitate formed during the mixing and aging of the solution is preferably separated from the liquid solution by any means known in the art such as, for example, filtering. The separated solid coprecipitate is then preferably washed to remove trace amounts of the liquid solution therefrom. After washing, the solid coprecipitate is preferably dried at a temperature of from about 80° C. to about 200° C., more preferably from 100° C. to 140° C. for a period of from about 0.5 to about 10 hours, more preferably from about 1 to about 5 hours. Thereafter, the dried solid coprecipitate is preferably calcined at a temperature of from about 200° C. to about 600° C., more preferably from about 300° C. to about 400° C. for a period of from about 1 to about 20 hours, more preferably from about 2 to about 8 hours.

The calcined coprecipitate comprising copper, zinc, aluminum, and gallium is thereafter preferably physically mixed with the solid acid and the binder in appropriate proportions suitable for providing the inventive catalyst composition described in the first embodiment of the present invention. The solid coprecipitate is preferably crushed into fine particles prior to or during mixing with the solid acid and binder. Water can be added during the physical mixing of the solid coprecipitate, solid acid catalyst, and binder to thereby form a paste capable of being shaped into suitable catalyst particles. Preferably, the paste is thereafter extruded into extrudate having a diameter of from about 1/16 to about 1/8 of an inch. Other suitable methods of shaping such as, for example, granulizing, pelletizing, and sphering may also be employed.

After shaping the mixture of solid coprecipitate, solid acid, and binder, the shaped catalyst is preferably dried at a temperature of from about 80° C. to about 200° C. for a period of from about 1 to about 10 hours. The dried catalyst is then calcined at a temperature of from about 200° C. to about 600° C., preferably from 300° C. to 400° C., for a period of from about 1 to about 10 hours, preferably from 3 to 7 hours.

After calcining, the catalyst is preferably reduced under conditions sufficient to reduce the valence of the copper component of the catalyst. Preferably, reduction is accomplished by contacting the catalyst with hydrogen at a temperature of from about 180° C. to about 320° C., preferably from 200° C. to 280° C., for a period of from about 0.5 to about 20 hours, preferably from 2 to 8 hours.

In accordance with a third embodiment of the present invention a process for converting carbon dioxide to oxygenates using the inventive catalyst composition described in the first embodiment of the present invention is provided.

The catalyst described and prepared in accordance with the first and second embodiments of the present invention can be employed to convert a feed containing carbon dioxide into oxygenates under any suitable conditions effective to promote such conversion. The carbon dioxide-containing feed and catalyst can be contacted in the reaction zone of any suitable reactor known in the art such as, for example, a fixed bed reactor, a moving bed reactor, a fluidized bed reactor, and transport reactors. Preferably, the inventive catalyst and the carbon dioxide-containing feed are contacted in a fixed bed reactor.

The carbon dioxide-containing feed contacted with the inventive catalyst composition preferably comprises hydrogen and carbon dioxide in amounts such that the hydrogen to carbon dioxide volume ratio ($H_2:CO_2$) of the feed is in the range of from about 0.1:1 to about 100:1, more preferably from about 1:1 to about 50:1, and most preferably from 5:1 to 15:1. Although the carbon dioxide-containing feed can contain trace amounts of other compounds such as, for example, carbon monoxide, it is preferred that the carbon dioxide-containing feed consist essentially of hydrogen and carbon dioxide. Preferably, the volume percent of carbon dioxide in the carbon dioxide-containing feed is from about 1 to about 50 volume percent by volume of the total carbon dioxide-containing feed, more preferably from about 5 to about 20 volume percent, and most preferably from 8 to 15 volume percent. The volume of hydrogen contained in the carbon dioxide-containing feed is preferably from about 50 to about 99 volume percent hydrogen based on the total volume of the carbon dioxide-containing feed, more preferably from about 70 to about 95 volume percent hydrogen, and most preferably from 85 to 95 volume percent hydrogen.

The carbon dioxide-containing feed preferably comprises less than about 20 volume percent of compounds other than carbon dioxide and hydrogen based on the total volume of the carbon dioxide-containing feed, more preferably less than about 10 volume percent of compounds other than carbon dioxide and hydrogen, even more preferably less than 2 volume percent of compounds other than carbon dioxide and hydrogen.

The rate at which the carbon dioxide-containing feed is charged to the reactor can be any rate suitable for promoting the conversion of carbon dioxide to oxygenates, particularly dimethyl ether. Preferably, the gas hourly space velocity (GHSV) of the carbon dioxide-containing feed charged to the reactor is in the range of from about 100 to about 20,000 $hr^{-1}$, more preferably from 1,000 to 5,000 $hr^{-1}$.

The temperature and pressure at which the reaction zone of the reactor is maintained can be any temperature and pressure which optimizes the conversion of carbon dioxide to oxygenates, particularly dimethyl ether. The reaction zone is preferably maintained at a temperature of from about 150°

C. to about 500° C., more preferably from about 200° C. to about 400° C., and most preferably from 250° C. to 320° C. The pressure in the reaction zone is preferably from about 200 psig to about 5,000 psig, more preferably from about 500 psig to about 4,000 psig, and most preferably from 1,200 psig to 1,600 psig.

After contacting the carbon dioxide-containing feed and the catalyst composition under reaction conditions, the oxygenate products can be recovered from the reactor by any suitable means known in the art.

The product of the reaction preferably comprises dimethyl ether (DME), methanol, and carbon monoxide. The amount of DME in the product as a mole percentage of all the carbon in the product is preferably greater than about 5 carbon mole percent, more preferably greater than about 20 carbon mole percent, and most preferably greater than 60 carbon mole percent. The amount of methanol in the product as a mole percentage of all the carbon in the product is preferably less than about 50 carbon mole percent, most preferably less than 25 carbon mole percent. The amount of carbon monoxide in the product as a mole percentage of all the carbon in the product is preferably less than about 20 carbon mole percent, more preferably less than about 10 carbon mole percent, and most preferably less than 5 carbon mole percent.

EXAMPLE I

Catalyst A (control) was prepared by combining 22.0 grams of copper nitrate ($Cu(NO_3)_2 \cdot 2½ H_2O$), 14.07 grams of zinc nitrate ($Zn(NO_3)_2 \cdot 6H_2O$), 2.95 grams of aluminum nitrate ($Al(NO_3)_2 \cdot 9H_2O$), 2.16 grams of gallium nitrate ($Ga(NO_3)_2 \cdot H_2O$), and 200 ml of water to form a metal-salt solution. A basic solution containing 20 grams of sodium carbonate ($Na_2CO_3$) and 200 ml of water was prepared separately. The metal-salt solution and the basic solution were then simultaneously added to a mixer containing 100 ml of water at 70° C. over a period of about 30 minutes while the mixer was agitating. The mixer was then turned off and its contents were allowed to age at 70° C. for about 1 hour. The solid coprecipitate substance formed in the mixer was then filtered from the liquid contents of the mixer and washed with water. The washed coprecipitate was placed in an oven and dried at 120° C. for about 3 hours. The dried coprecipitate was then calcined by raising the oven temperature to 350° C. for about 5 hours. The resulting 11.90 gram quantity of the calcined coprecipitate was designated Coprecipitate X.

A 3.0 gram quantity of Coprecipitate X was then crushed into a powder and mixed with 0.3 grams of bentonite. Water was slowly added to the mixture during mixing to form a paste. The paste was extruded with a syringe into extrudate having a diameter of approximately 1/16 inch. The extrudate was placed in an oven and dried at 120° C. for about 3 hours. The dried extrudate was then calcined by raising the oven temperature to 350° C. for 3 hours. The resulting calcined extrudate was designated Catalyst A.

Catalyst B (inventive) was prepared by mixing a 5.95 gram quantity of Coprecipitate X, described above, a 5 gram quantity of ZSM-5 zeolite (Zeocat PZ2/50H powder, provided by CU Chemie Uetikon AG, Uetikon, Switzerland), and a 1.5 gram quantity of bentonite. An 11.5 ml quantity of water was slowly added to the mixture during mixing to form a paste. The paste was then extruded, dried, and calcined in the same manner as described above with respect to the preparation of Catalyst A. The resulting calcined extrudate was designated Catalyst B.

EXAMPLE II

Catalyst A (control) was reactor tested by placing 2.5 grams of Catalyst A in a stainless steel tube reactor (I.D.=1 cm; length=60 cm). Catalyst A was reduced by charging hydrogen at about 50 cc/min to the reactor while maintaining the reactor at a temperature of about 240° C. After reduction, a feed of carbon dioxide and hydrogen having a $H_2/CO_2$ volume ratio of 9 was charged to the reactor at a GHSV of 2650 $hr^{-1}$ while the reactor was maintained at a temperature of 280° C. and a pressure of 1400 psig. Effluent samples were taken in 5 increments over a period of about 4.5 hours.

Catalyst B (inventive) was reactor tested by placing 4.75 grams of Catalyst B in the same reactor as was used to test Catalyst B. Catalyst B was then reduced and reacted with the same $H_2/CO_2$ feed employed for Catalyst A in substantially the same manner as described above with respect to Catalyst A. Effluent samples were taken at 6 increments over a period of about 6.5 hours.

The effluent samples from the reactor tests of Catalysts A and B were analyzed by gas chromatograph to determine average $CO_2$ conversion (%) and product selectivity (carbon mole %) to CO, methanol, and dimethyl ether.

TABLE 1

| Catalyst | $CO_2$ Conversion (%) | Product Selectivity (Carbon mole %) | | |
|---|---|---|---|---|
| | | CO | Methanol | Dimethyl Ether |
| A | 56.6 | 16.0 | 83.2 | 0.2 |
| B | 72.1 | 4.6 | 20.1 | 75.0 |

Table 1 illustrates that a Cu/Zn/Al/Ga catalyst including a solid acid component (Catalyst B) provides superior $CO_2$ conversion and dimethyl ether selectivity versus a Cu/Zn/Al/Ga catalyst that does not include a solid acid component (Catalyst A).

Reasonable variations, modifications, and adaptations can be made within the scope of this disclosure and the appended claims without departing from the scope of this invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process for converting a carbon dioxide-containing feed into oxygenates, said process comprising the steps of:
    (a) contacting said carbon dioxide-containing feed with a catalyst composition comprising a solid acid in a reaction zone under reaction conditions sufficient to convert at least a portion of said feed stream into oxygenates, said carbon dioxide-containing feed comprising at least 90 volume percent carbon dioxide and hydrogen, said solid acid comprising a zeolite; and
    (b) recovering at least a portion of said oxygenates from said reaction zone.

2. A process according to claim 1, said catalyst composition comprising gallium.

3. A process according to claim 1, said carbon dioxide-containing feed comprising at least 98 volume percent carbon dioxide and hydrogen.

4. A process according to claim 3, said catalyst composition comprising gallium and copper.

5. A process according to claim 1,
said carbon dioxide-containing feed consisting essentially of carbon dioxide and hydrogen.

6. A process according to claim 5,
said catalyst composition comprising gallium, copper, zinc, and aluminum.

7. A process according to claim 1,
said feed comprising carbon dioxide and hydrogen in a volume ratio of about 1:1 to about 50:1.

8. A process according to claim 1,
said oxygenates comprising dimethyl ether.

9. A process for converting a carbon dioxide-containing feed into oxygenates, said process comprising the steps of:
(a) contacting said carbon dioxide-containing feed with a catalyst composition comprising copper, zinc, aluminum, gallium, and a solid acid comprising a zeolite in a reaction zone under reaction conditions sufficient to convert at least a portion of said carbon dioxide-containing feed into oxygenates; and
(b) recovering at least a portion of said oxygenates from said reaction zone.

10. A process according to claim 9, said solid acid comprising ZSM-5.

11. A process according to claim 9,
said reaction conditions including a temperature of from about 50° C. to about 500° C. and a pressure of from about 200 psig to about 5,000 psig.

12. A process according to claim 9,
said carbon dioxide-containing feed being charged to said reaction zone at a GHSV of from about 100 to about 20,000 hr-1.

13. A process according to claim 9,
said carbon dioxide-containing feed consisting essentially of carbon dioxide and hydrogen.

14. A process according to claim 9,
said carbon dioxide-containing feed further comprising hydrogen.

15. A process according to claim 14,
said carbon dioxide-containing feed comprising said hydrogen and said carbon dioxide in amounts such that the volume ratio of said hydrogen to said carbon dioxide of said feed is in the range of from about 0.1:1 to about 100.1.

16. A process according to claim 15,
said carbon dioxide-containing feed comprising said carbon dioxide in an amount in the range of from about 1 to about 50 volume percent by volume of the total carbon dioxide-containing feed.

17. A process according to claim 16,
said carbon dioxide-containing feed comprising said hydrogen in an amount in the range of from about 50 to about 99 volume percent by volume of the total carbon dioxide-containing feed.

18. A process according to claim 17,
said carbon dioxide-containing feed comprising compounds other than carbon dioxide and hydrogen in an amount which is less than about 20 volume percent by volume of the total carbon dioxide-containing feed.

19. A process for converting a carbon dioxide-containing feed stream into oxygenates, said process comprising the steps of:
(a) contacting said feed stream with a catlyst composition comprising gallium and a solid acid comprising zeolite in a reaction zone under reaction conditions sufficient to convert at least a portion of said feed stream into oxygenates, said feed stream comprising carbon dioxide and hydrogen in a volume ration of about 0.1:1 to about 100:1, and said feed stream comprising less than about 20 volume percent of components other than hydrogen and carbon dioxide; and
(b) recovering at least a portion of said oxygenates from said reaction zone.

20. A process according to claim 19,
said feed stream comprising carbon dioxide and hydrogen in a volume ratio of about 1:1 to about 50:1.

21. A process according to claim 19,
said feed stream comprising carbon dioxide and hydrogen in a volume ration of 5:1 to 15:1.

22. A process according to claim 19,
said feed stream comprising less than about 10 volume percent of components other than carbon dioxide and hydrogen.

23. A process according to claim 19,
said feed stream comprising less than 2 volume percent of components other than carbon dioxide and hydrogen.

24. A process according to claim 19,
said feed stream consisting essentially of carbon dioxide and hydrogen.

25. A process according to claim 19,
step (a) including reacting carbon dioxide with hydrogen to thereby produce said oxygenates.

26. A process according to claim 19,
said oxygenates comprising dimethyl ether.

27. A process according to claim 19,
said catalyst composition comprising copper.

28. A process according to claim 27,
said catalyst composition comprising zinc.

29. A process according to claim 28,
said catalyst composition comprising aluminum.

30. A process for converting a carbon dioxide-containing feed into oxygenates, said process comprising the steps of:
(a) contacting said carbon dioxide-containing feed with a catalyst composition comprising a gallium and a solid acid comprising a zeolite in a reaction zone under reaction conditions sufficient to convert at least a portion of said feed stream into a product stream comprising dimethyl ether.
(b) recovering at least a portion of said dimethyl ether from said reaction zone.

31. A process according to claim 30,
said carbon dioxide-containing feed comprising at least about 80 volume percent carbon dioxide and hydrogen,
said product stream comprising at least about 20 carbon mole percent dimethyl ether.

32. A process according to claim 31,
said product stream comprising less than about 50 carbon mole percent methanol.

33. A process according to claim 30,
said carbon dioxide containing feed comprising at least 98 volume percent carbon dioxide and hydrogen,
said product stream comprising at least 60 carbon mole percent dimethyl ether.

34. A process according to claim 33,
said product stream comprising less than 25 carbon mole percent methanol.

35. A process according to claim 30,
said carbon dioxide-containing feed consisting essentially of carbon dioxide and hydrogen.

36. A process according to claim 30,
step (a) including converting carbon dioxide into said dimethyl ether.

37. A process according to claim 30,
said catalyst composition comprising copper.

38. A process according to claim 37,
said catalyst composition comprising zinc.

39. A process according to claim 38,
said catalyst composition comprising aluminum.

* * * * *

UNITED STATES PATENT AND TRADEMARK OFFICE
CERTIFICATE OF CORRECTION

PATENT NO. : 7,273,893 B2 Page 1 of 1
APPLICATION NO. : 10/683974
DATED : September 25, 2007
INVENTOR(S) : Jianhua Yao and James B. Kimble It is certified that error appears in the above-identified patent and that said Letters Patent is hereby corrected as shown below:

Column 9, Claim 19, line 62, please delete "catlyst" and insert therefor -- catalyst --.
Column 9, Claim 19, line 67, please delete "ration" and insert therefor -- ratio --

Signed and Sealed this

Fourth Day of December, 2007

JON W. DUDAS
*Director of the United States Patent and Trademark Office*